United States Patent [19]
Mongelli et al.

[11] Patent Number: 5,719,265
[45] Date of Patent: Feb. 17, 1998

[54] POLYMER-BOUND PACLITAXEL DERIVATIVES

[75] Inventors: Nicola Mongelli; Francesco Angelucci, both of Milan; Enrico Pesenti, Cologno Monzese; Antonino Suarato, Milan; Giovanni Biasoli, Gavirate, all of Italy

[73] Assignee: Pharmacia & Upjohn S.P.A., Milan, Italy

[21] Appl. No.: 508,209

[22] Filed: Jul. 27, 1995

Related U.S. Application Data

[62] Division of Ser. No. 263,832, Jun. 22, 1994, Pat. No. 5,473,055, which is a division of Ser. No. 077,065, Jun. 16, 1993, Pat. No. 5,362,831.

[30] Foreign Application Priority Data

Jun. 19, 1992 [GB] United Kingdom .................. 9213077

[51] Int. Cl.$^6$ ...................................... A61K 38/04
[52] U.S. Cl. ................ 530/329; 424/78.08; 424/78.13
[58] Field of Search .................... 530/329; 424/78.08, 424/78.13

[56] References Cited

U.S. PATENT DOCUMENTS 5,362,831  11/1994  Mongelli et al. ................. 526/304
5,473,055  12/1995  Mongelli et al. ................. 530/329

*Primary Examiner*—Thurman K. Page
*Attorney, Agent, or Firm*—Oblon, Spivak, McClelland, Maier & Neustadt, P.C.

[57] ABSTRACT

A polymer conjugate consisting essentially of: from 90 to 99.9 mol % of units represented by the formula

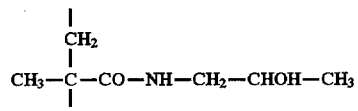

from 0.1 to 5 mol % of units represented by the formula

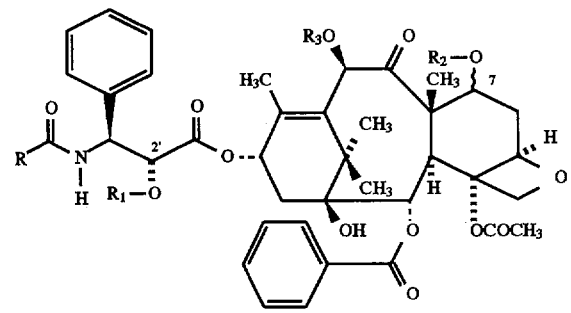

wherein one of $R_1$ and $R_2$ is a copolymer residue of the formula

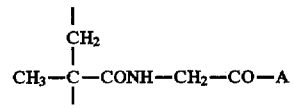

and the other one is hydrogen atom; from 0 to 9.9 mol % of units represented by the formula

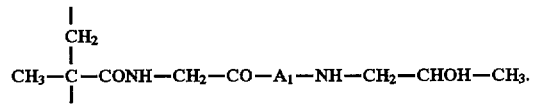

1 Claim, No Drawings

POLYMER-BOUND PACLITAXEL DERIVATIVES

This is a Division of application Ser. No. 08/263,832 filed on Jun. 22, 1994, now U.S. Pat. No. 5,473,055, which is a Division of application Ser. No. 08/077,065, filed Jun. 16, 1993, now U.S. Pat. No. 5,362,831.

The present invention is directed to polymer-bound paclitaxel and polymer-bound paclitaxel derivatives endowed with antitumor activity, to a method for their preparation and to pharmaceutical compositions containing them.

Paclitaxel (also named Taxol in several publications) is a member of the taxane family of diterpenes, isolated and characterized from an extract of bark of *Taxus brevifolia L.*; other analogues of paclitaxel are also known and were prepared by semisynthesis starting from 10-deacetyl baccatin III, extracted from the needles of *Taxus baccata L.*, see Wain et al. in JACS, 93, 2325 (1971) and Lovelle et al., Proc. Am. Assoc. Cancer Res., 31, p. 417, (1990). These compounds have been shown to possess potent antitumor activity, but they are very slightly soluble in water and some toxic side-effects are associated also with their administration by injection or intravenous infusion using as carrier cremophor EL (TM).

The present invention provides a polymer conjugate of the formula I consisting essentially of:
from 90 to 99.9 mol % of units of the formula:

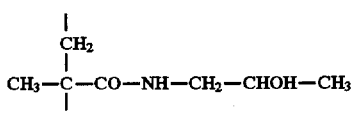

from 0.1 to 5 mol % units represented by the formula

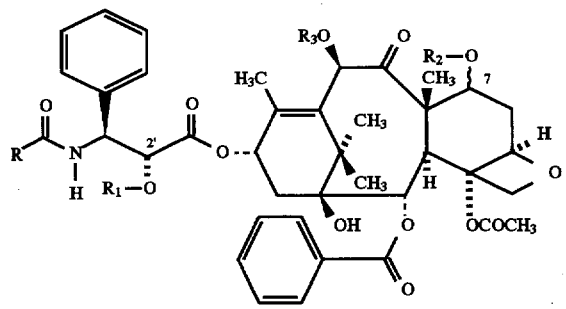

wherein one of $R_1$ and $R_2$ is a copolymer residue of the formula

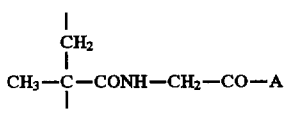

and the other one is hydrogen atom;
from 0 to 9.9 mol % of units represented by the formula

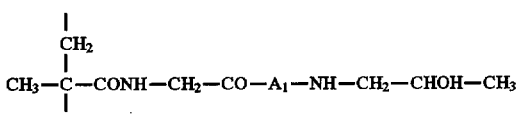

wherein R is a phenyl or t-butoxy group, $R_3$ is H or an acetyl group, A and $A_1$ which may be the same or different, represent a chemical single bond, an amino acid residue or peptide spacer selected from βAla, Gly, Phe-Gly, Phe-Phe-, Leu-Gly, Val-Ala, Phe-Ala, Leu-Phe, Leu-Ala, Phe-Leu-Gly, Phe-Phe-Leu, Leu-Leu-Gly, Phe-Tyr-Ala, Phe-Gly-Phe, Phe-Phe-Gly, Phe-Leu-Gly-Phe, Gly-Phe-Leu-Gly-Phe,Gly-βAla, Phe-Gly-βAla, Phe-Phe-βAla, Leu-Gly-βAla, Val-Ala-βAla, Phe-Ala-βAla, Leu-Phe-βAla, Leu-Gly-βAla, Phe-Leu-Gly-βAla,Phe-Phe-Leu βAla,Leu-Leu-Gly-βAla, Phe-Tyr-Ala-βAla, Phe-Gly-Phe-β, Phe-Phe-Gly-βAla, Phe-Leu-Gly-Phe-βAla or Gly-Phe-Leu-Gly-Phe-βAla.

More particularly the present invention provides polymer conjugates of paclitaxel and derivatives of paclitaxel with improved water solubility and decreased toxicity.

Preferably, the mol % of units containing the paclitaxel and paclitaxel derivatives is from 0.5 to 2, more preferably, the content of paclitaxel in the polymer was from 2 to 10% (w/w), most preferred compounds are those characterized by a content of from 4 to 7% (w/w). The wavy line denotes that the oxygen linked at position 7 of the paclitaxel structure may be in both configurations, i.e. β (natural) or α.

Preferably R represents a phenyl group, $R_3$ is an acetyl group and A is a Phe-Leu-Gly or Phe-Leu-Gly-βAla residue. All the amino acid residues have the natural L-configuration. According to a preferred embodiment, the polymer conjugate is a copolymer of 1-methacryloylamino-2-hydroxypropane, (methacryloylglycyl-phenylalanylleucylglycyl)3-amino-2 hydroxypropane and 2'-(methacryloylglycylphenylalanylleucylglycyl-βalanyl) paclitaxel.

The % w/w content was determined after enzymatic hydrolysis by HPLC method analogous to that described in Cancer Treatment Rep. 71 (1), 1987, p. 53–59.

Enzymatic hydrolysis

To 1 ml of murine or human plasmas various concentrations of the polymer-bound paclitaxel were added and at appropriate time (24, 48, 72, 96 h) 100 µl were collected and stored at −70° C. until further processing.

Extraction procedure

Samples were extracted by adding 75 µl of Tetra Butyl Ammonium Phosphate (TBAP) 0.5M, 1250 µl CH$_3$CN and 150 µl of NaCl 5M and vigorously shacked for 20' at 4° C.

After that time samples were spun at 15000×g for 10' and the supernatants were collected and evaporated using a high vacuum centrifuge. Samples were recovered by adding 500 µl of MeOH:H$_2$O (75:25 V/V) and injected into HPLC for determining the total paclitaxel percentage content.

| HPLC system | |
|---|---|
| Column | Nova Pak C$_{18}$ (Waters) 3.9 × 300 mm |
| Flow Rate | 1.5 ml/m |
| Detector | UV 231 nm |

-continued

| HPLC system | |
|---|---|
| Injection | 20 μl |
| Mobile Phase | 57.5% H₂O brought to pH 2 |
| | 42.5% CH₃CN |

The present invention also provides a process for preparing a polymer conjugate which process comprises reacting a compound of the formula II

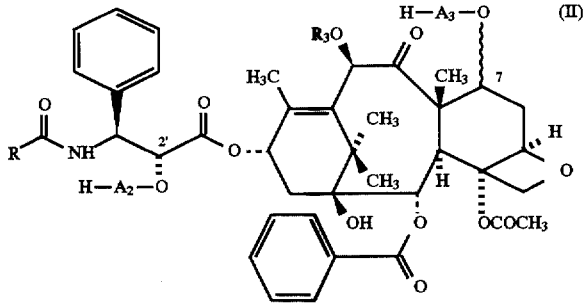

wherein one of $A_2$ and $A_3$ is a chemical bond and the other one is A, and A, R and $R_3$ are as defined above, with an activated polymer consisting essentially of from 90 to 99.9 mol % of units represented by formula

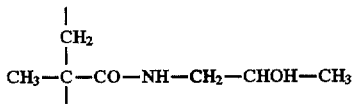

and from 10 to 0.1 mol % of units represented by the formula

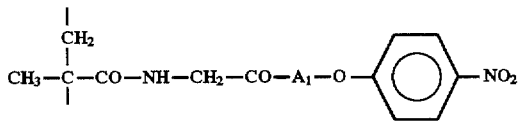

wherein $A_1$ is as defined above and then treating the resultant polymer conjugate with 2-hydroxypropylamine.

Preferably the reaction between the compounds of the formula II and the activated polymer is carried out in an anhydrous polar organic solvent such as dimethylsulfoxide or dimethylformamide optionally in presence of an organic or inorganic base such as an alkaline carbonate, dimethylaminopyridine or triethylamine. The reaction can typically be effected for from 1 to 24 hours.

The reaction is typically carried out at a temperature of from 15° to 40° C., preferably at room temperature. The alkaline carbonate is, for example, an alkali metal carbonate or an alkaline earth metal carbonate.

Some of the starting compounds of the formula II are known compounds, i.e. paclitaxel or paclitaxel analogues or may be prepared starting from known compounds.

For example 7-epi derivatives may be prepared by refluxing in toluene paclitaxel or its analogs in the presence of a base ($Na_2CO_3$ or diazabicycloundecene)

Other compounds of the formula II are new, in particular those in which $A_3$ is βAla residue and those in which either $A_2$ or $A_3$ represents di, tri, or tetra peptide spacer as defined above for A and are within the scope of the invention.

The compounds of formula II wherein $A_2$ is not a chemical single bond may be prepared by reacting a paclitaxel or a paclitaxel analog with protected amino acid or peptide in the presence of a condensating reagent, and with or without the additional presence of a catalyst, preferably at room temperature, followed by the removal of the protecting group with known methods.

The condensation may be also carried out using activated esters such as paranitrophenyl ester of peptide or amino acid. Suitable condensing reagents include carbodiimides such as dicyclohexyl carbodiimide (DCC).

Suitable catalysts include 4-dimethylamino-pyridine (DMAP), pyridine or triethylamine.

Various known amino protecting groups can be utilized and commercially available protected amino acid or peptides can be utilized as the starting materials. Amino acids or peptides protected with t-BOC, trityl, FMOC or carbobenzyloxy (CBZ) can be utilized. Amino Acid or peptides procted with t-BOC, trityl or FMOC groups are preferred.

The compounds of the formula II wherein $A_3$ is not a chemical single bond may be prepared by protecting or blocking the 2'-hydroxy group and then esterifying the 7-position hydroxyl and then removing the 2'-protecting or blocking group.

More preferably, the compounds of the formula II wherein $A_3$ is Gly or βAla residue are prepared by reacting paclitaxel with 2–3 equivalents of N-protected amino acid to produce 2',7-disubstituted paclitaxel, the 2'-position amino acid is cleaved and then the 7-position amino acid is deprotected.

Reaction of paclitaxel and the protected amino acid is conducted in the presence of a condensing reagent and a catalyst, like those above defined.

Cleavage of the 2'-amino acid is conducted by adjusting the pH of the 2'-7-(amino acid) paclitaxel solution to pH 7–7.4 for example by mixture of the 2',7-di(amino acid) paclitaxel in a phosphate buffer at pH 7–7.4 or with a slight excess of $NaHCO_3$.

Deprotection of the amino acid is conducted under a known amino acid deprotection method, such as mild acid treatment with, for example, acetic acid, or by reduction.

Thus, for example, paclitaxel is allowed to react with 2–3 mol. equivalent of N-protected amino acid (t.boc, CBZ or FMOC protected) in methylene chloride in the presence of DCC and a catalytic amount of 4-dimethylaminopyridine. In this manner, the protected amino acid is introduced at 2' and 7-position. The 2',7-bis amino acid derivative of paclitaxel is allowed to stand in presence of $NaHCO_3$ in $H_2O$/MeOH for 2–5 hours, whereby selective deprotection at the 2'-position occurs to yield the 7-substituted derivative of paclitaxel. The protecting groups are removed by appropriate deprotecting agent (e.g., acid, mild base or hydrogenolysis).

The activated polymer is a synthetic, water soluble polymer prepared by the copolymerization of N'-(2-hydroxypropyl) methacrylamide with p-nitrophenylesters of N-methacryloyl oligopeptides, as described in U.S. Pat. No. 4,062,831 and U.S. Pat. No. 4,097,470.

The polymer conjugates of the formula I and the new paclitaxel derivatives of the formula II exhibit good water solubility, biocompatibility and release the paclitaxel or paclitaxel derivative in the plasma or after internalization into cells by cleaving of the oligopeptide spacers.

Biological activity

Microtubule assembly and disassembly assay

Calf brain tubulin was prepared by two cycles of assembly-disassembly (Shelanski M. L. Gaskin F. and Cantor C. R., Proc. Natl. Acad. Sci. U.S.A. 70, 765–768, 1973) and stored in liquid nitrogen in MAB (0.1M MES, 2.5 mM EGTA, 0.5 mM MgSO₄, 0.1 mM EDTA, 0.1 mM DTT pH 6.4). All the experiments were carried out on protein stored for less than 4 weeks.

Before each experiment, the tubulin was kept 30 min at 4° C.

Assembly was monitored by the method of Gaskin et al (Gaskin F., Cantor C. R. Shelanski M. L. J. Molec. Biol 89, 737–758, 1974). The cuvette (1 cm path) containing tubulin (1 mg/ml) and 1 mM GTP was shifted to 37° C. and continous turbidity measurements were made at 340 nm on Perkin-Elmer 557 Double Wavelenght Double Beam Spectrophotometer equipped with an automatic recorder and a termostatically regulated sample chamber.

After 30 minutes 4 mM CaCl₂ was added and depolymerisation was measured for 10 minutes as decreased turbidity. At regular intervals of 15 minutes scalar doses of the tested compounds were added and variations in the turbidity were monitored. Data are espressed as percentage of ripolymerisation induced by the tested compounds. The results are shown in Table I.

In vitro drug sensitivity assay

Exponentially growing B16-F10 murine melanoma cells were seeded (2×10⁴/ml) in RPMI 1640 medium were supplemented with 10% heat-inactivated fetal calf serum and 2 mM glutamine in 24 well-plates (Costar). Scalar concentrations of tested compounds were added immediately after seeding. The inhibition of cell growth was evaluated by counting cells with a coulter counter after 72 hrs incubation. For each tested compound concentration triplicate cultures were used. The antiproliferative activity of the tested compounds was calculated from dose-response curves and espressed as $IC_{50}$ (dose causing 50% inhibition cell growth in treated cultures relative to untreated controls). The result are shown in Table I.

TABLE I

| Compound prepared in | Tubulin Assembly % | | |
|---|---|---|---|
| | 0.5μM | 5μM | $IC_{50}$ (μM) |
| Example 1 | 0 | 15 | 19 |
| Example 9 | 79 | 145 | 47 |
| Example 3 | 46 | 86 | 23 |
| Example 4 | 0 | 10 | 11 |
| Example 6 | 0 | 10 | 51 |
| Reference compound: | | | |
| Paclitaxel | 41 | 96 | 39 |

The copolymer-paclitaxel prepared in Example 6 was tested in vivo against B16 F10 murine melanoma in comparison with paclitaxel.

Mice

C57B16 female mice were obtained from Charles River Italy.

Animals were 8 to 10 weeks old at the beginning of the experiment.

Drugs

Because of its limited aqueous solubility, paclitaxel was dissolved in a vehicle consisting of polyoxyethylated castor oil (Cremophor EL) 50% and ethanol 50% and then diluted with glucose 5% solution at the desidered concentrations. The solution was slightly hazy and precipitates formation was observed after short time.

The compound of example 6 was easily dissolved in glucose 5% and the resulting solution was clear for long time (more than 2 hours). Final concentrations were referred to the paclitaxel content of the compound (4% of total).

Tumor

The murine melanoma B16F10 was used. A suspension of 10⁵ tumor cells in 0.2 ml was injected subcutaneously in the flank of mice.

Tumor size was measured with caliper and tumor weight was calculated with the formula:

$$\frac{a^2 + b}{2}$$

Drugs administration

Paclitaxel was given intraperitoneally because of its poor solubility and vehicle toxicity.

The compound of example 6 was injected intravenously. Both compounds were administered at day 1, 5, 9 after tumor implantation.

The data reported in Table 2 show that the compound of the present invention is more active than paclitaxel.

The dose of the polymer-conjugate is referred to the paclitaxel content.

TABLE 2

| Compound | Dose (mg/Kg) | Tumor Inhibition (%) | Tox |
|---|---|---|---|
| Control | — | — | — |
| Paclitaxel | 14.6 | 53 | 0/10 |
| | 22 | 38 | 0/10 |
| | 33 | 92 | 1/7 |
| Compound of ex. 6 | 14.6 | 77 | 0/9 |
| | 22 | 79 | 0/10 |

TOX determination was made when mice died before the control or when significant body weight loss and/or spleen and or/or liver size reduction were observed.

From the above data, it can be seen that the polymer conjugates of the present invention exhibit excellent antitumor activity. These compounds, therefore, are useful antitumor agents due to the lower toxicity and increased water solubility as compared to paclitaxel or its derivative. Examples of tumors that can be treated are for istance, sarcomas, carcinoma, lymphomas, neuroblastoma, melanoma, myeloma, Wilms tumor, leukemias and adenocarcinoma.

The improved solubility ad decreased toxicity of the polymer-conjugates of the present invention means that they are suitable for intravenous injection or infusion. The dosage depends upon the age, weight and condition of the patient. The dosage may be from 1 mg/kg body weight to 1 g/kg body weight, preferably from 4 to 800 mg/kg body weight. Typical formulations contain a quantity of polymer-bound paclitaxel/polymerbound paclitaxel derivative equivalent to 0.5, 1.5, 10, 20, 25, or 50 mg of the active paclitaxel/paclitaxel derivative.

The polymer conjugates may be formulated as pharmaceutical compositions with a pharmaceutically acceptable carrier or diluent. Any appropriate carrier or diluent may be used. The solutions for intravenous injection or infusion may contain as carrier or diluent, for example, sterile water or preferably they may be in the form of sterile, aqueous or isotonic saline solutions.

The following examples illustrate the invention.

EXAMPLE 1

Copolymer of 1-Methacryloylamino-2-hydroxypropane, 1 (Methacryloyl-glycyl-phenylalanyl-leucyl-glycyl)amino-2-hydroxypropane and 2'(Methacryloyl-glycyl-phenyl-alanyl-leucyl-glycyl)paclitaxel To a solution of 1.4 g of copolymer of 1-methacryloylamino-2-hydroxypropane and N-(methylencarbonyl-Phe-Leu-Gly 4-nitrophenoxy) methacrylamide, prepared according to J. Kopecek et al., Makromol Chem 177, p. 2833 (1976), in 15 ml of anhydrous dimethylformamide were added 100 mg of paclitaxel and 15 mg of dimethylaminopyridine.

The yellow solution was stirred for 8 hours at room temperature under anhydrous conditions. Then 2-hydroxy propylamine (0.2 ml) was dropped into reaction flask, and then the whole was stirred for 30 minutes.

The reaction solution was quenched with 0.3 ml glacial acetic acid, concentrated under vacuum to a small volume, and then poured into 200 ml of acetone.

After 30' mixing, the precipitate was filtered and washed with acetone to yield 1.25 g of the title compound.

The paclitaxel content was 4.5% (evaluated by enzymatic hydrolysis and HPLC analysis).

Unreacted paclitaxel was recovered from acetone solution.

EXAMPLE 2

2'(N-trityl-phenylalanyl-leucyl-glycyl)paclitaxel

To a solution of 170 mg of paclitaxel in 16 ml of acetonitrile were added 24 mg of dimethylamino-pyridine and 150 mg of N-trityl-phenylanyl-leucyl-glycine 4-nitrophenyl ester.

The yellow solution was stirred for 20 hours at room temperature, and then evaporated under vacuum to dryness. The residue was cromatographed on silica gel with ethyl-acetate-hexane 35:25 as eluant, affording 380 mg of the title compound.

H-NMR(400 MHz, CDCl$_3$): δ0.82 (d, J=6.4 Hz, 3H, δ-Leu), 0.85 (d, J=6.7 Hz, 3H, δ-Leu), 1.15 (s, 3H, 16), 1.26 (s, 3H, 17), 1.2–1.6 (m. 3H, β+β+γ-Leu), 1.69 (s, 3H, 19), 1.85 (s, 1H, OH-1), 1.89 (m, 1H, 6β), 1.96 (d, J=1.2 HZ, 3H, 18), 2.14 (dd, J=5.9 Hz, J=13.5 Hz, 1H, β-Phe), 2.24 (s, 3H, CH$_3$CO-10), 2.2–2.7 (m, 5H, CH$_2$-14+OH-7+6α+βPhe+ NH-Phe), 2.47 (s, 3H, CH$_3$CO-4), 3.50 (m, 1H, α-Phe), 3.74 (dd, J=4.7 Hz, J=18.2 Hz, 1H, α-Gly), 3.80 (m, 1H, α-Leu), 3.83 (d, J=7.0 Hz, 1H, 3), 4.17 (dd, J=7.0 Hz, J=18.2 Hz, 1H, α'-Gly), 4.22, 4.33 (two-d, J=8.5 Hz, 2H, CH$_2$-20), 4.46 (m, 1H, 7), 4.97 (dd, J=2.2 Hz, J=9.9 Hz, 1H, 5), 5.44 (d, J=2.3 Hz, 1H, 2'), 5.71 (d, J=7.0 Hz, 1H, 2), 5.97 (dd, J=4.7 Hz, J=7.0 Hz, 1H, NH-Gly), 6.07 (dd, J=2.3 Hz, J=9.4 Hz, 1H, 3'), 6.2–6.3 (m. 2H, 13+10), 6.8–9.2 (m, 30 H, 6-Ph), 6.95 (d, J=6.7 Hz, 1H, NH-Leu), 8.00 (d, J=9.4 Hz, 1H, NH-4').

EXAMPLE 3

2'(Phenylalanyl-leucyl-glycyl)paclitaxel

The compound 2'(N-Trit-Phe-Leu-Gly)paclitaxel (250 mg) was dissolved into a mixture of glacial acetic (22 ml) and water (6 ml) and the whole was stirred for 1 hour at room temperature.

The solvents were evaporated in vacuum to the dryness, the residue stirred with diethylether-hexane 1:1 for 30 minutes and filtered to obtain 160 mg of the title compound.

FAB-MS: m/z 1171, M +H ]$^+$; 1112, M -CH$_3$COOH+2H; 1051, 1024, 911, 603, 569, 509. $^1$H-NMR (400 MHz, CDCl$_3$): δ0.88(d,J=6.4 Hz,3H, δLeu), 0.92(d,J=6.4 Hz,3H, δ'Leu), 1.13 (s, 3H, 16), 1.16 (s, 3H, 17), 1.4–2.0 (m, 4H, β+β'+γLeu+6β), 1.69 (s,3H, 19), 1.91 (d,J=1.2 Hz,3H,18), 2.16 (dd, J=6.0 Hz,J=13.8 Hz,1H,14), 2.23 (s, 3H, COCH$_3$-10), 2.4–2.6 (m, 3H, 6α+14+βPhe), 2.53 (s,3H,COCH$_3$-4), 2.90 (dd, J=4.1 Hz, J=13.5 Hz, 1H,β'-Phe), 3.49 (dd, J=4.1 Hz, J=9.1 Hz,1H, αPhe), 3.82 (d, J=7.3 Hz,1H,3), 3.9–4.1 (m,2H,α+α'Gly), 4.22, 4.33 (two-d, J=8.7 Hz, 2H, CH$_2$-20), 4.27 (m, 1H, α-Leu), 4.44 (dd, J=6.4 Hz, J=10.8 Hz,7), 4.98 (dd, J=2.4 Hz, J=9.7 Hz,5), 5.61 (d, J=3.2 Hz,1H,2'), 5.70 (d, J=7.3 Hz,1H,2), 6.12 (dd,J=3.2 Hz,J=9.4 Hz,1H,3'), 6.21 (m, 1H, 13), 6.28 (s,1H,10), 6.8–8.2 (m,21H,4-Ph+NHLeu), 7.87 (d,J=9.4 Hz,1H,NH-4').

EXAMPLE 4

Copolymer of 1-Methacryloylamino-2-hydroxypropane, 1-(Methacryloyl-glycyl)amino-2-hydroxypropane and 2'(Methacryloyl-glycyl-phenylalanyl-leucyl-glycyl)paclitaxel To a solution of 1 g of copolymer of 1-methacryloylamino-2-hydroxypropane and N-(methylencarbonyl-4-nitrophenoxy)methacrylamide, prepared according to P. Rejmanova et al., Makromol. Chem. 178, p. 2159–2168, in 10 ml of anhydro dimethylformamide were added 100 mg of 2' Phe-Leu-Gly-paclitaxel and 10 mg of dimethylaminopyridine.

The yellow solution was stirred for 2 hours at room temperature under anhydrous conditions. Then 2-hydroxypropylamine (0.15 ml) was added to the reaction solution, and the whole was stirred for 30 minutes. The reaction solution was quenched with 0.2 ml of glacial acetic acid, concentrated under vacuum to a small volume and then poured into 200 ml of acetone.

The mixture was stirred for 1 hours, the precipitate was filtered and washed with acetone to yield 960 mg of the title compound.

The paclitaxel content was 6% (evaluated by enzymatic hydrolysis and HPLC analysis).

EXAMPLE 5

Copolymer of 1-Methacryloylamino-2-hydroxypropane, 1(Methacryloyl-glycyl)amino-2-hydroxypropane and 2'(Methacryloyl-glycyl) paclitaxel To a solution of 1.6 g of copolymer of 1-methacryloylamino-2-hydroxypropane and N-(methylen-carbonyl-4-nitrophenoxy)methacrylamide in 16 ml of anhydrous dimethylformamide were added 100 mg of paclitaxel and 20 mg of dimethylamino-pyridine. The yellow solution was stirred for 20 hours at room temperature, then 2-hydroxypropylamine (0.2 ml) was added, and the whole was stirred for 30 minutes. The reaction solution was quenched with 0.3 ml of glacial acetic acid, concentrated under vacuum to a small volume, and then poured into 200 ml of acetone. The mixture was stirred for 1 hour, the precipitate was filtered and washed with acetone to yield 1440 mg of the title compound.

The paclitaxel content was 2.75% w/w %

EXAMPLE 6

Copolymer of 1-Methacryloylamino-2-hydroxypropane, 1-(Methacryloyl-glycyl-phenylanyl-leucyl-glycyl)amino-2-hydroxypropane and 2'(Methacryloyl-glycyl-phenylalanyl-leucyl-glycyl-βalanyl)paclitaxel To a solution of 620 mg of copolymer of 1-metacrylamino-2-hydroxypropane and N-(methylencarbonyl-Phe-Leu-Gly-4'-nitro-phenoxy)

methacrylamide in 6 ml of anhydrous dimethyl-formamide were added 62 mg of 2'-(βalanyl)paclitaxel, prepared according to N. F. Magri et al, J Nat. Products 51 298–306, 1988, and 10 mg of dimethylamino pyridine. The yellow solution was stirred for 5 hours at room temperature under anhydrous conditions.

Then 2-hydroxypropylamine (0.1 ml) was added and the whole was stirred for 30 minutes.

The reaction solution was quenched with 0,15 ml of glacial acetic acid, concentrated under vacuum to a small volume and poured in 150 ml of acetone. The mixure was stirred for 1 hour, the precipitate was filtered and washed with acetone to yield 5.85 mg of the title compound.

The paclitaxel content was 4% w/w %

EXAMPLE 7

2',7-Di(carbobenzyloxy-β-alanyl)paclitaxel

To a solution of 200 mg of paclitaxel in 15 ml of acetonitrile were added 400 mg of N,N'-dicyclohexylcarbodiimide, 200 mg of carbobenzyloxy-β-alanine and 60 mg of dimethylamino-pyridine. The reaction mixture was stirred for 20 hours, the precipitate was filtered and the solvent evaporated under vacuum to dryness.

The residue was chromatographed on silica gel with ethyl acetate-hexane 1:1 as eluant, affording 300 mg of the title compound.

FAB-MS: m/z 1264 M+H]$^+$, 1204, 1130, 1070.

EXAMPLE 8

7-(Carbobenzyloxy-βalanyl)paclitaxel

To a solution of 171 mg of 2'7-di(carbobenzyloxy-β-alanyl)paclitaxel in 60 ml of methanol, were added 30 mg of sodium bicarbonate and 7 ml of water. The reaction mixture was stirred for 3 hours at room temperature.

The methanol was evaporated and the product extracted with ethylacetate.

The solvent was evaporated under vacuum to dryness, affording 134 mg of the title compound.

EXAMPLE 9

7-(βAlanyl)paclitaxel

To a solution of 135 mg of 7-(carbobenzyloxy-βalanyl) paclitaxel in 20 ml of methanol and 13 ml of formic acid, was added 200 mg of Pd/C 5%. The reaction mixture was stirred for 6 hours at room temperature. The catalyst was filtered, washed with methanol and the solvents were evaporated to dryness under vacuum. The residue was dissolved in 8 ml of methanol and precipitated with 150 ml of diethylether, affording 85 mg of the title compound.

FAB-MS: M/z 925, M+H]$^+$; 947, M+Na]$^+$ $^1$H NMR (400 MHz, CDCl$_3$): δ1.14 (s,3H,CH$_3$-16), 1.20(s,3H,CH$_3$-17), 1.79 (s,3H,CH$_3$-19), 1.85 (s, 3H,CH$_3$-18), 2.17 (s, 3H,CH$_3$CO-10), 2.2–2.6 (m, 6H, CH$_2$-14+CH$_2$-6+OCOCH$_2$ C$\underline{H}_2$NH$_2$), 2.42 (s, 3H, CH$_3$CO-4), 3.0–3.2 (m,2H,OCOCH$_2$ C$\underline{H}_2$NH$_2$), 3.90 (d,J=6.8 Hz,1H,3), 4.18, 4.31(two d, J=8.2 Hz,2H,CH$_2$-20), 4.80 (d,J=3.2 Hz,1H,2'), 4.91 (d,J=8.5 Hz,1H,5), 5.62(dd,J=10.2 Hz, J=7.0 Hz,1H,7), 5.66 (d,J=6.8 Hz,1H,2), 5.81(dd,J=2.9 Hz, J=9.1 Hz,1H,3', 6.17 (m,1H, 13), 6.19 (s,1H,10), 7.3–8.2 (m,16H,NH-4'+3-Ph).

EXAMPLE 10

Copolymer of 1-Methacryloylamino-2-hydroxypropane, 1-(Methacryloyl-glycyl-phenylalanyl-leucyl-glycyl)amino-2-hyroxypropane and 7-(Methacryloyl-glycyl-phenylalanyl-leucyl-glycyl-βalanyl)paclitaxel To a solution of 1500 mg of copolymer of 1-methacryloylamino-2-hydroxypropane and N-(methylencarbonyl-Phe-Leu-Gly-4nitrophenoxy) methacrylamide in 13 ml of anhydrous dimethylformamide were added 135 mg of 7-(βalanyl)paclitaxel and 20 mg of dimethylaminopyridine.

The yellow solution was stirred under anhydrous conditions for 5 hours at room temperature.

Then 2-hydroxypropylamine (0.2 ml) was added, and the whole was stirred for 30 minutes.

The reaction solution was quenched with 0.3 ml of glacial acetic acid, concentrated under vacuum to a small volume and poured in 250 ml of acetone. The mixture was stirred for 1 hour, the precipitate was filtered and washed with acetone to yield 1520 mg of the title compound.

The paclitaxel content was 7.8% w/w %.

We claim:

1. A pharmaceutical composition comprising a pharmaceutically acceptable diluent or carrier and, as an active ingredient, a polymer conjugate selected from the group consisting of: (1) a copolymer of 1-methacryloylamino-2-hydroxypropane, 1-(methacryloylglycyl-phenylalanyl-leucyl-glycyl)-amino-2-hydroxypropane and 2'-(methacryloyl-glycyl-phenylalanyl-leucyl-glycyl-βalanyl) paclitaxel; (2) a copolymer of 1-methacryloylamino-2 -hydroxypropane, 1-(methylacryloyl-glycyl-phenylalanyl-leucyl-glycyl)amino-2-hydroxypropane and 2'-(methacryloyl-glycyl-phenylalanyl-leucyl-glycyl) paclitaxel; (3) a copolymer of 1-methacryloylamino-2-hydroxypropane, 1-(methacryloyl-glycyl)amino-2-hydroxypropane and 2'-(methacryloyl-glycyl-phenylalanyl-leucyl-glycyl)paclitaxel; and (4) a copolymer of 1-methacryloylamino-2-hydroxy-propane, 1-(methacryloyl-glycyl)amino-2-hydroxypropane and 2'-(methacryloyl-glycyl)paclitaxel.

* * * * *

UNITED STATES PATENT AND TRADEMARK OFFICE
CERTIFICATE OF CORRECTION

PATENT NO. : 5,719,265
DATED : February 17, 1998
INVENTOR(S) : Nicola MONGELLI, et al.

It is certified that error appears in the above-indentified patent and that said Letters Patent is hereby corrected as shown below:

On the title page, Item [*] is missing.  It should read:

--[*]   The term of this patent shall not extend
        beyond the expiration date of Pat. No.
        5,569,720.--

Signed and Sealed this

Nineteenth Day of May, 1998

Attest:

BRUCE LEHMAN

Attesting Officer      Commissioner of Patents and Trademarks